United States Patent
Jensen et al.

[11] Patent Number: 6,066,187
[45] Date of Patent: May 23, 2000

[54] SOLAR REDUCTION OF $CO_2$

[75] Inventors: Reed J. Jensen, 121 La Vista Dr., Los Alamos, N.Mex. 87544; John L. Lyman, Los Alamos, N.Mex.; Joe D. King, Los Alamos, N.Mex.; Robert D. Guettler, Los Alamos, N.Mex.

[73] Assignee: Reed J. Jensen, Los Alamos, N.Mex.

[21] Appl. No.: 09/034,873

[22] Filed: Mar. 4, 1998

Related U.S. Application Data

[60] Provisional application No. 60/038,576, Mar. 4, 1997.

[51] Int. Cl.[7] .................... C10J 3/20; B01J 19/08
[52] U.S. Cl. .................... 48/85; 422/186; 422/186.3
[58] Field of Search .................... 422/186, 186.3; 252/373; 423/418.2; 48/85, 197

[56] References Cited

U.S. PATENT DOCUMENTS

| | | | |
|---|---|---|---|
| 4,062,348 | 12/1977 | Morrison | 126/714 |
| 4,064,024 | 12/1977 | Lee | 204/157.44 |
| 4,405,594 | 9/1983 | Pyle | 423/579 |

OTHER PUBLICATIONS

B.R. Lewis and J.H. Carver, in J. Quant. Spectrosc. Radiat. Transfer 30, 297 (1983).
K. Yoshino et al., in J. Quant Spectrose. Radiat. Transfer 55, 53 (1996).
J. W. Rablais et al., Chem. Rev. 71, 73(1971).
D. E. Shemansky, J. Chem. Phys. 56, 1582 (1972).
M. Koshi et al., Chem. Phys. Lett. 176, 519 (1991).
N. A. Generalov et al., Opt. Spectrosc. 15, 12 (1963).
R. N. Dixon, Proc. Roy. Soc. 275, 431 (1963).
C. Cossart–Magos et al., Mol. Phys. 75, 835 (1992).
K.L. Coulson, Solar and Terrestrial Radiation: Methods and Measurements, Academic Press, New York (1975), p. 40.

*Primary Examiner*—Marian C. Knode
*Assistant Examiner*—Alexa A. Doroshenk
*Attorney, Agent, or Firm*—Samuel M. Freund

[57] ABSTRACT

The red shift of the absorption spectrum of $CO_2$ with increasing temperature permits the use of sunlight to photolyze $CO_2$ to CO. The process of the present invention includes: preheating $CO_2$ to near 1800 K; exposing the preheated $CO_2$ to sunlight, whereby CO, $O_2$ and O are produced; and cooling the hot product mix by rapid admixture with room temperature $CO_2$. The excess thermal energy may be used to produce electricity and to heat additional $CO_2$ for subsequent process steps. The product CO may be used to generate $H_2$ by the shift reaction or to synthesize methanol.

10 Claims, 5 Drawing Sheets

SOLAR REDUCTION OF CO₂

This application claims the benefit of U.S. Provisional Application No. 60/038,576 Filing Date Mar. 4, 1997.

This invention was made with government support under Contract No. W-7405-ENG-36 awarded by the U.S. Department of Energy to The Regents of the University of California. The government has certain rights in the invention.

FIELD OF THE INVENTION

The present invention relates generally to the red shift in the ultraviolet absorption spectrum of $CO_2$ into the blue end of the solar spectrum with increasing temperature and, more particularly, to the use of this effect for the direct solar reduction of $CO_2$ for removing and recycling this atmospheric greenhouse gas.

BACKGROUND OF THE INVENTION

Present reserves of fossil fuel result from the storage of ancient solar energy as chemical energy. As these reserves are combusted, the attendant growth in the atmospheric and oceanic reservoirs of $CO_2$ contributes to the greenhouse effect. There has been a general recognition of the need for an efficient process to assist natural processes in photochemically removing $CO_2$, while storing solar energy. Ongoing developments in solar fuels involve either biological processes or hydrogen production from water splitting. No known research addresses the problem directly through the physical and spectral properties of $CO_2$. It has been noted in the literature that $CO_2$ has no spectral absorption in the visible or near-ultraviolet portion of the spectrum under normal circumstances; therefore, direct photoreduction of $CO_2$ has appeared to be unlikely and has received little attention.

FIG. 1 hereof, labeled prior art, shows existing measurements of the temperature dependence of the $CO_2$ absorption spectrum. The dotted and solid curves were reported by B. R. Lewis and J. H. Carver, in J. Quant. Spectrosc. Radiat. Transfer 30, 297 (1983), at 202 and 367 K, respectively. Some temperature dependence was observed throughout the entire spectral range, but the greatest effect was at longer wavelengths. The absorption cross sections were found to increase with temperature at about 1.5%/K at the long wavelength limit of these data sets (197 nm). K. Yoshino et al., in J. Quant Spectrosc. Radiat. Transfer 55, 53 (1996), measured the same spectrum at two temperatures (195 K and 295 K) between 120 and 175 nm. Their results were nearly identical to those of Lewis and Carver, supra. These results suggest that substantial enhancement of absorption cross section may be expected at longer wavelengths and elevated temperatures. The spectrum published by J. W. Rablais et al. in Chem. Rev. 71, 73 (1971) and the measurement of D. E. Shemansky in J. Chem. Phys. 56,1582 (1972) agree with the room temperature data of Lewis and Carver, supra, in the region of overlap. Shemansky, supra, extended the measurement out to 300 nm where extinction by Rayleigh scattering interfered with observation of the very weak absorption.

M. Koshi et al. in Chem. Phys. Lett. 176, 519 (1991) reported a dramatic increase in the absorption of $CO_2$ with temperature between 1500 and 3000 K. The absorption cross sections at 193 nm were inferred in shock-heated $CO_2$ by measuring the atomic oxygen produced by photolysis of $CO_2$. The determination of absorption cross sections assumed a unity photolysis quantum yield to $O(^3P)$ atoms. Measurements at 1520 K and 2850 K are also shown in FIG. 1 as circles and squares, respectively. N. A. Generalov et al. in Opt. Spectrosc. 15, 12 (1963) measured the absorption of $CO_2$ behind a shock wave at temperatures as high as 6300 K for wavelengths of 238 and 300 nm. Absorption out to 355 nm at 5000 K was observed. Although the reported data are not precise, an increase of absorption with temperature is indicated. Cross sections and error estimates were derived by the present inventors from the data at 1523 K, 1818 K, 2073 K, and 2273 K. The results for 2273 K are shown as triangles in FIG. 1.

The visible emission seen by many in carbon monoxide/oxygen flames is evidence that transitions exist for $CO_2$ to absorb visible and near ultraviolet light if the molecule is heated sufficiently. This emission has been studied between 310 and 380 nm in R. N. Dixon, Proc. Roy. Soc. 275, 431 (1963), and the conclusion was drawn that it came from transitions between the bent $^1B_2$ state of $CO_2$ to highly excited vibrational states of the electronic ($^1\Sigma_g^+$) ground state. Thermal population of the highly excited vibrational states at high temperatures should allow absorption, the reverse of this emission process, to occur. To reach the absorption transitions observed by Dixon, supra, in emission would require vibrational energy in excess of 1.88 eV. At room temperature, the fraction of molecules with more than 1.88 eV is $7\times10^{-30}$. However, that fraction is $1.3\times10^{-4}$ at 1523 K and $8.8\times10^{-3}$ at 2273 K. Transitions to the $^1A_2$ state may also contribute to absorption by $CO_2$. C. Cossart-Magos et al., in Mol. Phys. 75, 835 (1992) have attributed nine weak bands between 175 and 200 nm to transitions to that state. Similar transitions from vibrationally excited states could contribute to the absorption spectrum at longer wavelengths and elevated temperatures.

Direct solar reduction of $CO_2$ would require significant absorption cross section beyond 300 nm as is illustrated in FIG. 1, where a portion of the solar irradiance at the earth's surface taken from *Solar and Terrestrial Radiation: Methods and Measurements* by K. L. Coulson, Academic Press, New York (1975), p. 40, is shown.

Accordingly, it is an object of the present invention to provide a process for the direct solar reduction of $CO_2$ to CO.

Another object of the present invention is to provide a process for generating CO and hydrogen for liquid fuel production from $CO_2$ in the ambient atmosphere.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method for generating carbon monoxide from carbon dioxide hereof includes: heating flowing carbon dioxide to a temperature such that absorption of the solar spectrum occurs; exposing the heated carbon dioxide to solar radiation whereby substantial dissociation of the carbon dioxide to carbon monoxide takes place, forming thereby a hot gas mixture; and cooling the hot gas mixture sufficiently rapidly to stabilize the carbon monoxide.

Benefits and advantages of the present invention include the preparation of liquid fuel while removing an important greenhouse gas from the atmosphere.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings.

DETAILED DESCRIPTION

Briefly, the present invention includes the extension of the spectral absorption cross sections from the ultraviolet into the solar region of the spectrum for hot $CO_2$. Such absorption either produces direct dissociation of $CO_2$ into CO+O or raises the temperature of the gas, thereby increasing thermal dissociation. The dissociation products can then be used to create synthesis gas ($CO+H_2$) for the production of liquid fuels. Thus, the proposed process reduces combustion $CO_2$ emissions, closes the carbon fuel cycle, and creates a class of solar fuel products.

Figure 1:
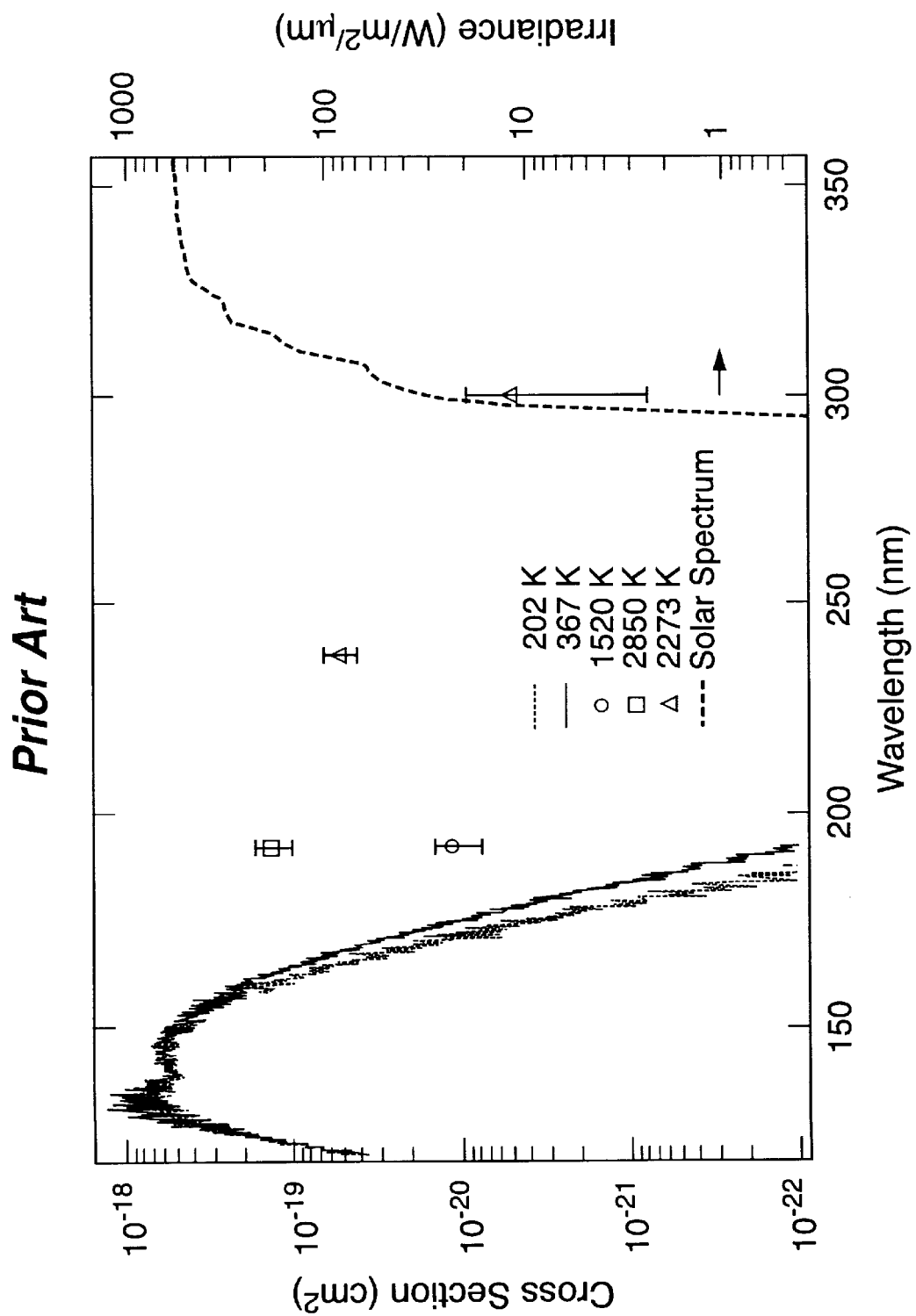
FIG. 1 shows prior art absorption cross sections for $CO_2$ as a function of wavelength at various temperatures. The solar irradiance (dashed line, right axis) is also shown.
Figure 2:
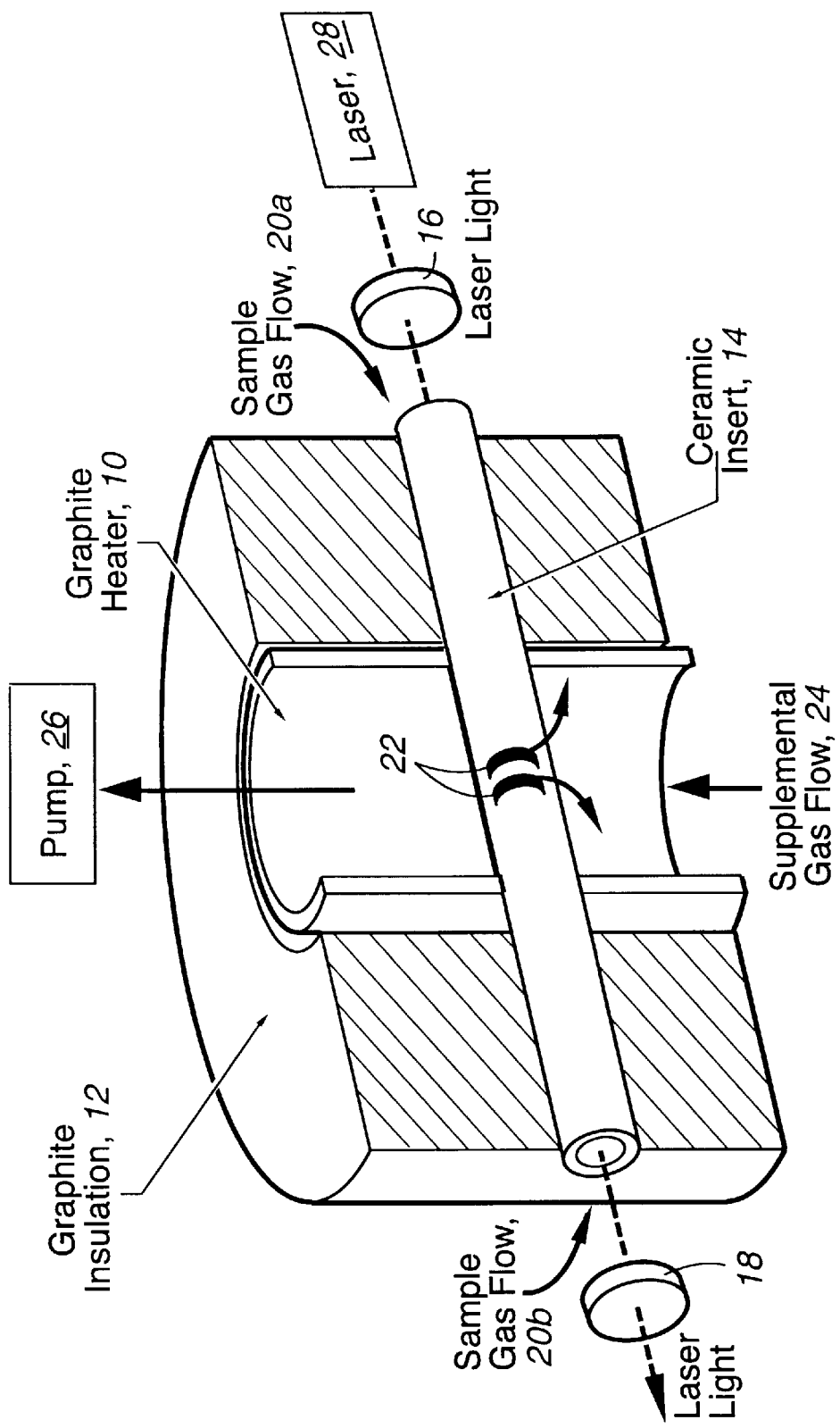
FIG. 2 is a schematic representation of a heated cell in which the absorption measurements for $CO_2$ of the present invention were performed.

Reference will now be made in detail to the present embodiment of the invention, an example of which is illustrated in the accompanying drawings. In order to generate the absorption cross sections required to demonstrate the method of the present invention and to go beyond the transient shock environment of Generalov et al., supra, carbon dioxide was heated in a commercial electrical furnace, a schematic representation of which is shown in FIG. 2 hereof. Resistive heater element, 10, and insulation, 12, of the furnace were both constructed out of graphite. At high temperatures, however, $CO_2$ will react with graphite to make CO. At temperatures above 1500 K the $CO_2$, CO, and graphite equilibrium strongly favors CO ($CO_2$:CO<1:1000). To minimize the loss of $CO_2$ in this apparatus, an yttria ceramic insert, 14, was used to assist in the isolation of the $CO_2$ from the hot graphite furnace elements. The insert connects the optical path entrance and exit windows, 16 and 18, respectively. Sample gas, 20a and 20b, was introduced into the furnace at the window ports where it flows across the inside window surfaces. The gas then flows down the length of the tube and out through slits, 22, near the center. The ceramic insert limits the operating temperature of the apparatus to 2273 K, at which temperature the insert showed signs of fracture and loss of rigidity. Because the hot graphite readily reduces $CO_2$ to CO, the environment outside the ceramic insert is almost entirely CO. By maintaining a constant positive flow rate of $CO_2$ into the ceramic insert, however, the back-flow of CO into the insert through the center slits was minimized. The furnace was operated under steady-state flow conditions. Along with gas flow into the window ports, a small amount of gas, 24, was introduced through a secondary inlet to regulate the total cell pressure. An adjustable flow to a source of vacuum, 26, is the only gas outlet. Cell pressures were nominally maintained at about 300 torr.

The gas composition inside the ceramic insert was determined by taking gas samples at several points along the length of the insert at 1808 K. Mass spectrometric analyses of these samples showed that the $CO_2$ fraction along the observation path varied from 83 to 94%. Carbon monoxide was the primary constituent in the remaining fraction. The $CO_2$ partial pressure was taken to be 90% of the total cell pressure for all of the experimental data presented.

The entrance and exit windows of the optical path were separated by approximately 36 cm. The graphite heater element was at the center and directly heated approximately 6 cm of this path length. In the 15-cm distance between the window and the heater element, the temperature rose from room temperature to the furnace operating temperature. The gas temperature down the length of this tube was measured, providing an experimental temperature profile. This temperature profile complicated the assignment of an experimental path length and gas density, as will be discussed more fully hereinbelow.

The transmission spectra were measured using the tunable ultraviolet output of a laser apparatus, 28, which produces pulses at 10 Hz through a substantial portion of the visible and ultraviolet regions. The pulse energies ranged between 0.2 and 0.5 mJ with spectral widths between 6 and 30 $cm^{-1}$ and a temporal width of 10 ns. In the temperature range of interest, 1523 to 2273 K, absorption measurements require a probe beam that is significantly brighter than the thermal background radiation. The laser source employed provided ample brightness for these measurements. The incident and transmitted energies were measured for each laser shot. Ten laser shots were averaged by a radiometer, which was read three times for each wavelength. The scan reproducibility of the laser system is believed to be the major contributor to the noise in the measured data. The $CO_2$ absorption spectra were determined by first filling the hot cell with helium and measuring the background transmission spectrum over the desired range, typically 230 to 344 nm. The cell was then evacuated to ≈10 torr, filled with $CO_2$, and the transmission spectrum of the $CO_2$ measured. The cell was again evacuated, filled with helium, and another background transmission spectrum was measured. Whenever possible, the sample transmission spectrum was corrected with the average of the before and after background measurements.

A more sensitive method was used to measure the $CO_2$ transmission at selected wavelengths. With the laser wavelength fixed and the cell initially filled with helium, the transmission was continuously measured at intervals of approximately 3 s. While monitoring the transmission, the cell was evacuated and filled with $CO_2$. After allowing the transmission to stabilize, the cell was evacuated and again filled with helium. Several data points from these absorption curves were averaged to determine the background and sample transmission and, with these averages, the sample transmission was corrected for the background. These absorption "step" scans have significantly better sensitivity than the laser scan methods described above, providing absorption sensitivity down to 0.003, or approximately $5 \times 10^{-22}$ $cm^2$ cross section. This limit is somewhat wavelength dependent and primarily results from pointing instabilities in the laser system.

Carbon monoxide and molecular oxygen are two impurities that could contribute to the measured $CO_2$ absorption. Absorption in the Shuman-Runge bands of $O_2$ extends down to at least 230 nm at high temperatures, but the absorption cross sections for this trace contaminant are too low to affect the absorption. Although up to 17% (probably less than 10%) of the probed gas might be CO, the impact of CO on the absorption is also expected to be negligible. Carbon monoxide only absorbs in the region of interest in the weak, narrow Cameron bands which cannot account for the observed absorption. No detectable absorbence by CO in the range of 230 to 344 nm at 2073 K was found. However, at 2273 K and 355 nm, the absorption step measurements detected an absorbence for CO that was 30% of the $CO_2$ absorbence. The present inventors believe that this absorbence comes from the high-temperature conversion of $CO_2$ to CO, but if it comes from some other high-temperature contaminant, the cross section at 2273 K and 355 nm could be in error by as much as 30%.

Figure 3:
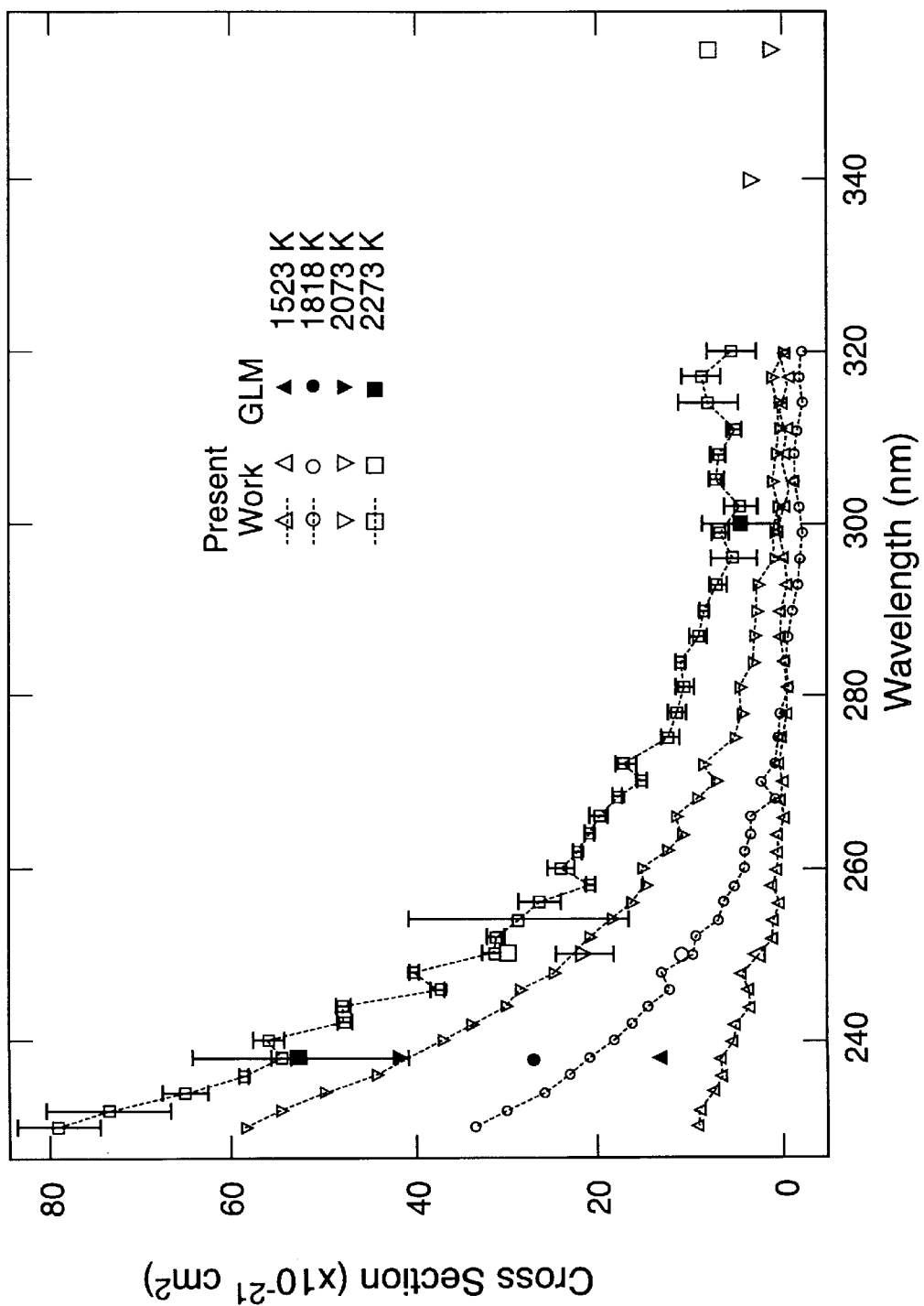
FIG. 3 shows absorption cross sections for $CO_2$ derived from measurements using the apparatus shown in FIG. 2 hereof.

To provide meaningful estimates of the absorption cross sections, the effect of the temperature profile along the optical path was deconvoluted from the measured absorption data using an iterative process. An initial estimate of the absorption cross section was made using the 6 cm, directly heated path length. Then the wavelength and temperature dependence of these cross sections was fitted. This cross section estimate as a function of temperature and wavelength was combined with the temperature profile of the furnace to calculate an expected absorbence. The ratio of this calculated absorbence to the experimentally observed absorbence was used to correct the cross section estimate. The procedure for the fitting of these corrected cross sections was repeated until the cross section estimates converged to within 1%. The final cross sections were used to find a set of "effective" path lengths that would transform the observed experimental absorbence into the calculated cross section at the experimental temperature and pressure. As expected, these effective path lengths depend on both the temperature and wavelength. This set of path lengths was then applied to the measured absorbence data. The resulting absorption cross section estimates for 1523 K, 1818 K, 2073 K, and 2273 K are shown in FIG. 3. The data presented at 1523 K and 2273 K are the result of single scans, while those at 1818 and 2073 K are the result of averaging two data scans. Error estimates ($\pm\sigma$) are included on the 2273 K absorption scan which had the largest error of the four scans. The same effective path lengths described above were used to correct the single wavelength measurements made at 250 nm and 340 nm. The absorbence at 355 nm was corrected with an effective path length extrapolated from the calculated values between 230 nm and 344 nm. The absorption cross section estimates for these three wavelengths are presented in Table 1. They are also included in FIG. 3 for comparison. Each of these values results from an average of two to four measurements. A representative error estimate ($\pm\sigma$) of these individual cross section measurements is included on FIG. 3 for the 2073 K data point at 250 nm.

TABLE 1

| Temperature (K.) | Wavelength (nm) | | |
| --- | --- | --- | --- |
| | 250 | 340 | 355 |
| 1523 | $2.9 \pm 0.1 \times 10^{-21}$ | | |
| 1818 | $1.1 \pm 0.3 \times 10^{-20}$ | | |
| 2073 | $2.2 \pm 0.3 \times 10^{-20}$ | $3.5 \pm 0.7 \times 10^{-21}$ | $1.5 \pm 0.3 \times 10^{-21}$ |
| 2273 | $3.0 \pm 0.1 \times 10^{-20}$ | | $8.4 \pm 0.4 \times 10^{-21}$ |

Some selected absorption cross sections from the shock wave measurements of Generalov et al., supra, are also included in FIG. 3. At 238 nm, cross sections are presented for 2273 K, 2073 K, 1818 K, and 1523 K. At 300 nm, the 2273 K measurement is presented. Representative error estimates resulting from the scatter in the shock-wave data are provided for the measurements at 2273 K. It may be observed that there is good agreement between the present results and the previous measurements at the higher temperatures (2273 K and 2073 K). At the lower temperatures, 1523 K and 1818 K, the discrepancy between the present measurements increases. Yet, even at these temperatures, the discrepancy is not greater than the error estimates of the shock-wave results.

In the process of the present invention for utilizing this absorption in $CO_2$ for direct photoreduction of $CO_2$, partially preheated $CO_2$ is introduced into an inverted funnel that concentrates the arriving, mirror-directed solar energy and the preheated $CO_2$ into a photolysis or dissociation zone. About 5% of the incoming solar energy will be directly absorbed on hollow metal vanes near the mouth of the funnel that supports the structure and heat the $CO_2$ as it is drawn into the funnel by a gas turbine or other pumping means located beyond the throat of the funnel. The remainder of the energy passes beyond the vanes to be absorbed in the hot gas further up the funnel.

The scale of the process is chosen to utilize hundreds of megawatts of solar radiation and has the potential to produce millions of liters per year of high quality liquid fuel. The funnel entrance is anticipated to be tens of square meters and its length near 10 meters. The opening at the funnel throat will be near 200 $cm^2$. The available absorption path length of hot $CO_2$ in the apparatus will be tens of meters so that a cross section in the range of $10^{-21}$ to $10^{-22}$ $cm^2$ is all that is required for a practical process. At present, it is not known whether the solar absorption is directly actinic or whether the absorption will simply lead to strong heating that will result in significant dissociation of $CO_2$ to CO.

After dissociation, adequate amounts of room-temperature $CO_2$ will be rapidly admixed to stabilize the CO and $O_2$ product and cool the gas to near 1600 K, where the gas is relatively stable. It will then be further cooled to near 500 K by extracting shaft energy using a gas turbine system or some other heat exchanger apparatus. The design mixing scheme would be aided by rather high, but subsonic flow rates along with an array of rapidly pulsed mixing jets. Solar intensity near $10^5$ suns will be required to process all of the gas at the design flow rates.

Separation of $O_2$ and $CO_2$ will yield a CO stream that, when combined with $H_2$ from the shift reaction, $CO + H_2O \rightarrow CO_2 + H_2$, will give a stream of synthesis gas that can be transformed into liquid fuel by standard processes.

Having generally described the invention, the following example will provide specific details of the implementation of the present method.

EXAMPLE

Figure 4:
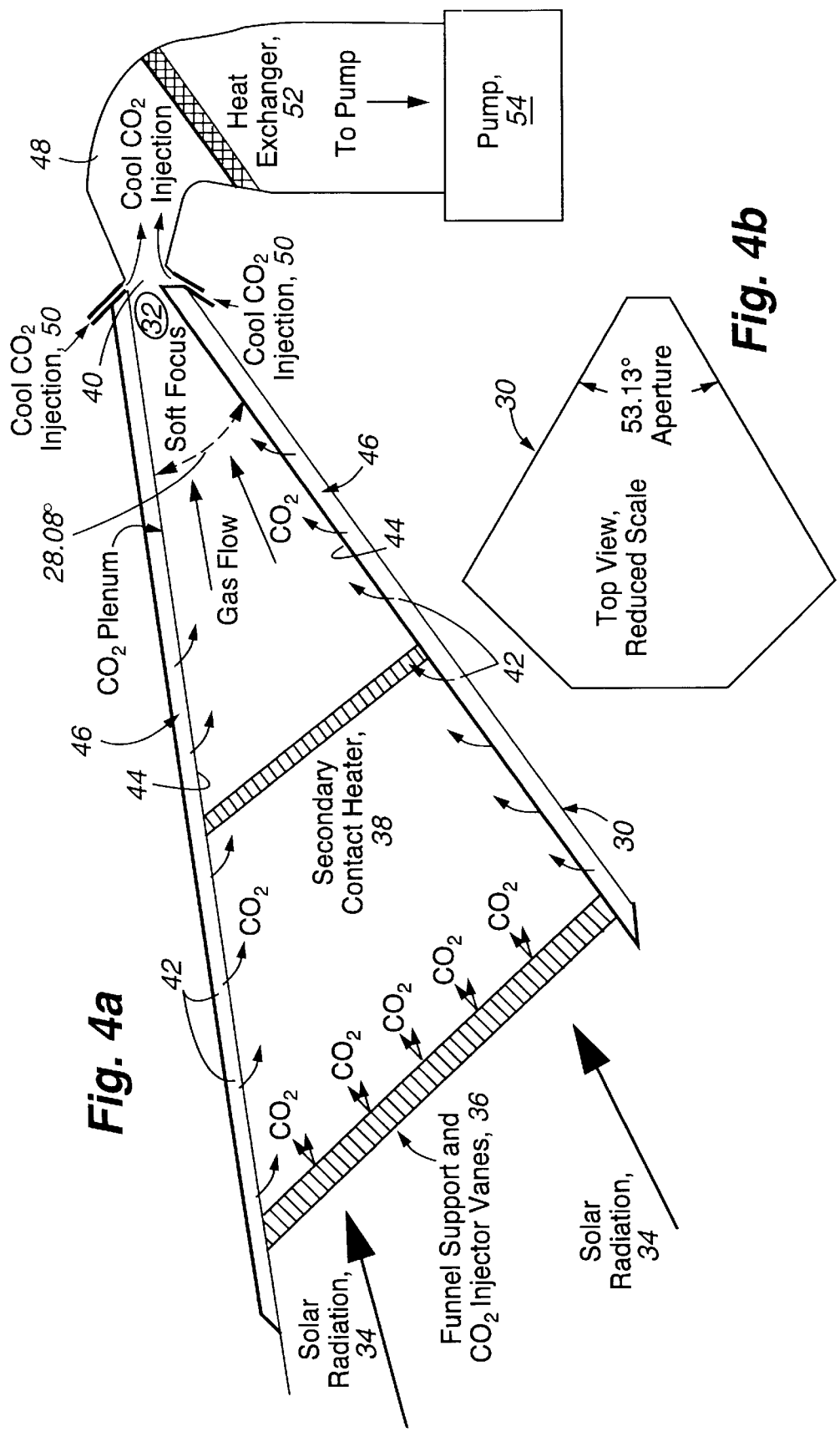
FIGS. 4a and 4b are schematic illustrations of the side planar view and the top planar view, respectively, of a solar funnel for demonstrating the method of the present invention, where solar irradiance and hot $CO_2$ are concentrated into a reaction plenum such that the $CO_2$ is exposed to a soft focus of solar radiation.

FIGS. 4a and 4b show the side view and the top view, respectively, of a solar funnel, 30, which concentrates solar power and hot $CO_2$ into a reaction plenum where the $CO_2$ will be exposed to a soft focus, 32, of solar radiation. No solar window is required because the $CO_2$ is introduced into the funnel at high temperatures where it is much lighter than air and will rise naturally into the funnel throat. Moreover, the $CO_2$ introduction rate will be balanced against the withdrawal rate from the funnel in order to prevent air from entering the funnel. The $CO_2$ is first removed from ambient air and heated before it is introduced into the funnel. It is anticipated that current membrane technology or soda lime chemistry will enable this separation to be inexpensively and readily accomplished. In the present design, the trapezoidal funnel opens at 28.08° in the vertical and 53.13° in the horizontal direction (FIG. 4b). These values were chosen for ease of design calculations and, clearly, other values might be employed. An intense solar radiation of 361 MW, 34, would be supplied by 433×10³ m² of concave mirror area deployed in a 60° circular sector 1500 m maximum distance from a 240 m high tower (Not shown in FIG. 4).

A plurality of hollow vanes, 36, near the entrance of the funnel serves four purposes: 1) to mechanically support and stabilize the structure; 2) to provide contact heating for the $CO_2$ by intercepting a portion of the incident sunlight and transferring it to the gas; 3) to inject hot $CO_2$ into the funnel; and 4) to stabilize the injected gas against being blown out of the funnel entrance by side winds. A second plurality of vanes, 38, 3 m further toward the throat, 40, of the funnel provides additional contact heating to raise the temperature of the $CO_2$ so that the direct absorption of solar energy is enabled.

In what follows, a funnel design will be set forth; however, there is substantial flexibility in the design presented. Many of the parameters can be changed by large factors with appropriate adjustments in others. Throat, 40, of the funnel is a slot 20 cm high by 1 m long for an area of 0.2 m². The flow area at distances down the funnel is shown in Table 2.

TABLE 2

| Distance down centerline (m) | 0 throat | 2 | 4 | 6 con- tact- or | 8 | 9 In- jec- tion | 10 |
|---|---|---|---|---|---|---|---|
| Vertical opening (m) | .2 | 1.2 | 2.2 | 3.2 | 4.2 | 4.7 | 5.2 |
| Horizontal opening (m) | 1.0 | 3 | 5 | 7 | 9 | 10 | 11 |
| Flow area (m²) | .2 | 3.6 | 11 | 22.4 | 37.8 | 47 | 57 |
| Flow velocity (m/s) | 371 | 20.6 | 6.75 | 3.31 | 1.96 | 1.58 | 0 |
| Time to transit a 10 cm vane (ms) | .27 | 4.8 | 14.8 | 30.2 | 51.0 | 63.3 | not applicable |

Flow speeds can be calculated at the various funnel positions by the familiar equation W=n A V, where W is the mass flow rate, n is the number density, A is the funnel area, and V is the gas velocity. The required mass flow to achieve a target production of, say, 50 million liters of methanol per year, with an assumed value of $n=3.3 \times 10^{24}$ m$^{-3}$, is 407 mole/sec, taking into account approximately 15% loss of product due to recombination and other internal losses. This yields $V=407 \times 6.02 \times 10^{23}$ s$^{-1}$/$3.3 \times 10^{24}$ A=74.25 m³ s$^{-1}$/A.

A. $CO_2$ Preheating

Carbon dioxide, heated to 1000 K, is also introduced through small orifices, 42, placed on a grid of approximately 1 cm in two dimensions in the funnel walls to cool the walls and heat the $CO_2$. One-fourth of the gas (102 moles/sec) is admitted through the funnel wall and ¾ (305 moles/sec) through the hollow vanes 36.

B. Funnel Support and Hot $CO_2$ Injection

The first heat exchanger (vanes 36) is located near the funnel entrance or about 9 m from funnel throat 40. Vanes are chosen to be 40 cm deep (in the flow direction) by 0.33 cm wide (inside bore) and aerodynamically smoothed inside and out, such that they absorb 4.87% of the incoming light or 17.5 MW. The vanes are wedge-shaped with most of the gas being injected toward the funnel entrance so that the gas will pass twice over the hot surface. One vertical vane is located every 10 cm, for 100 vanes. The total internal flow area is 40.3 cm×0.33 cm=16 cm²/vane×100 vanes or 1600 cm² total injector vane duct area and 400 m² heat-transfer area or 300 m² effective area, when realistic flow patterns are taken into account. This yields a flow speed of 348 m/sec for ¾ of the funnel flow, the remainder of the gas being introduced through the array of small holes in the funnel reflective walls.

The heat-transfer equation is: $dQ/dt = K A \Delta T$, where K is the heat-transfer coefficient (For $CO_2$, K is between 50 and 250 W m$^{-2}$ deg$^{-1}$ sec$^{-1}$). Because of the high temperatures involved, a value of 200 W m$^{-2}$ deg$^{-1}$ sec$^{-1}$ for this coefficient seems appropriate, A is the heat transfer area, $\Delta T$ is the temperature head and, t is the residence time. In the first stage, 17.5 MW is desired to be transferred to the gas entering the funnel. For this geometry, $\Delta T$ is calculated from:

$$17.5 \times 10^6 \text{ J sec}^{-1} = (200 \text{ J sec}^{-1} \text{ m}^{-2} \text{ deg}^{-1}) 300 \text{ m}^2 \Delta T,$$

from which $\Delta T=292°$ C. Taking into account the doubling back of the gas flow over the vanes, there is an effective doubling of the area (inside and out) which reduces the temperature head to 146° C. The emergence temperature of the $CO_2$ will be near 1900 K so the temperature of the vane material can be as low as 2100 K; Zr melts at 2125 K.

In summary, a funnel having 100 hollow vertical vanes, each 40 cm deep and 0.50 cm wide, that intercept 17.5 MW of light will heat the conducted $CO_2$ (305 moles per sec) to approximately 1900 K.

C. Second Contact Heater to Supply the Final 100° C. of Heating

The thermal head required to transfer the final $\Delta T$ of 100° C. for a set of thin vanes 38 every 10 cm at 7 m from the funnel throat is now calculated. $dQ/dt = K A \Delta T$ for a set of thin vanes every 10 cm (offset from the first set) 7 cm deep, with A=45 m², and $\Delta T=1.75 \times 10^6$ J sec$^{-1}$/(200 J sec$^{-1}$ m$^{-2}$ deg$^{-1}$)45 m²=200° C. The temperature vanes will therefore be about 2200 K, well within the range of many high temperature materials. These vanes need intercept only 1.0% of the light so they should be thin sheet construction. The second contactor thus consists of 80 vertical vanes (one every 10 cm) 7 cm deep and about 60 mil thick.

D. Heating Along the Funnel Walls

The funnel wall area, 44, between the injector and the throat is 84 m², and the transit time of gas through the funnel is 1.4 s for the ¼ of the gas that travels in this direction. Again, $dQ/dt = K A \Delta T$, so that $5.8 \times 10^6$ J sec$^{-1}$=(200 J sec$^{-1}$ m$^{-2}$ deg$^{-1}$)84 m² $\Delta T$, from which $\Delta T=350°$ C. Since there is a double pass across each side of the interior funnel walls (each of the funnel walls depicted in FIG. 4a is actually a duct, 46, which carries $CO_2$), $\Delta T=175°$ C.

For gas that is effused much closer to the focus, the $\Delta T$ will be higher, but probably not more than about 50° C. higher. The average ray suffers 4 or 5 bounces, principally at the smaller end of the funnel, before turn around so more heating is expected near the soft focus.

Thus, a design for preheating the gas and cooling selected parts of the funnel is achievable.

E. Quenching with Cool $CO_2$

Stabilizing the CO+O photolysis products against the back reaction to $CO_2$ is achieved by quenching, 48, with a five-fold excess of cool $CO_2$. Cooling occurs by direct heat transfer and by providing copious centers for the cooling reaction $CO_2+O=CO+O_2$. This reaction has a positive enthalpy of reaction of 4.6 kcal mole$^{-1}$ which provides cooling and additional CO. At temperatures over 2500 K the reaction is as fast or faster that the recombination reaction $CO+O=CO_2$. The rapid mixing of cool $CO_2$ assures that the reaction will have an appreciable effect. The cool $CO_2$ would be injected in such a way that strong turbulent mixing with attendant cooling by reaction and dilution occurs.

For a very simple, no turbulence case, simple Fick's law calculations (using a diffusion coefficient of 2.5 cm$^2$ sec$^{-1}$ for O atom at 3500 K) shows a diffusion rate of approximately 0.2 cm/ms. A more detailed two-dimensional computer simulation including mixing and CO stabilization shows the effectiveness of the method. The simple model employs the reactions:

$$CO+O=CO_2$$

$$O+O=O_2$$

$$CO_2+O=CO+O_2$$

and their reverse reactions, along with the implied gas dynamics and the mixing physics for a simple laminar confluence of the hot stream and the cool stream. The calculated situation was for a 1 to 1 mix, on a molar basis, of hot and cool gas. In practice a five-fold excess of cool gas will be added. More importantly, the model does not include realistic three-dimensional aspects of high velocity injection, mixing by turbulence or mixing by temporal bursts. In spite of these limitations, the model shows that at least half of the product CO and $O_2$ is preserved and that the about 0.16 mole fraction $O_2$ is preserved at a distance of 1.5 m downstream. The theoretical maximum for this case is 0.33 mole fraction. This is a rather unambiguous indication of the extent of stabilization that has been achieved, and it is strongly indicative that the introduction of three dimensional effects and burst-mode induced turbulence will stabilize most of the remaining CO and $O_2$.

Figure 5:
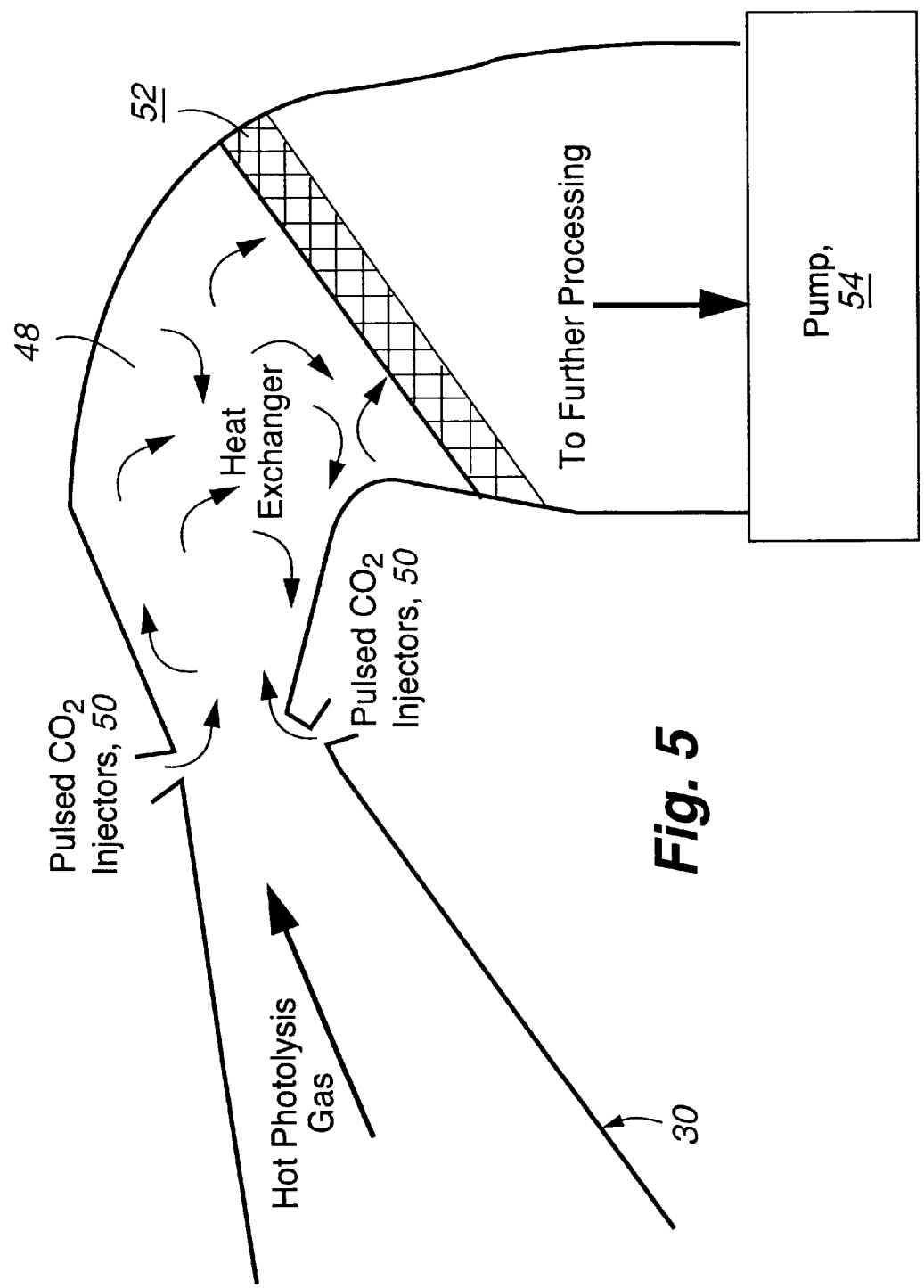
FIG. 5 is a schematic illustration of the injection of cool $CO_2$ into the hot reaction gases generated by the funnel shown in FIG. 4 hereof in such a manner that strong turbulent mixing rapidly cools the gases by reaction and dilution.

A set of high pressure, high velocity $CO_2$ injectors, 50, 10 along the top and 10 along the bottom, offset from each other spatially will provide the maximum amount of mixing as shown in FIG. 5. The injectors insert cool gas into the product stream at near sonic velocity to effect an entrainment of the 500 m/s hot gas stream and induce strong turbulence in the expanding duct. To further induce turbulence and mixing, the injectors will be mechanically or fluidically pulsed at rates near 1 kHz. This allows interfolding of the gas streams in small dimensions (10 to 50 cm) that are rapidly homogenized by strong turbulence. Additional cooling is achieved using heat exchanger, 52. The cooled, stabilized gases may then be collected for processing by use of pump, 54, which also ensures that all gases flow in the proper direction.

The foregoing description of the invention has been presented for purposes of illustration and description and is not intended to be exhaustive or to limit the invention to the precise form disclosed, and obviously many modifications and variations are possible in light of the above teaching. The embodiments was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for generating carbon monoxide from carbon dioxide, which comprises the steps of:
   (a) heating flowing carbon dioxide to a temperature such that absorption of the solar spectrum occurs;
   (b) exposing the heated carbon dioxide to solar radiation whereby dissociation of the carbon dioxide to carbon monoxide takes place, forming thereby a hot gas mixture; and
   (c) cooling the hot gas mixture to stabilize the carbon monoxide.

2. The method for generating carbon monoxide from carbon dioxide as described in claim 1, wherein said step of heating the flowing carbon dioxide to a temperature such that absorption of the solar spectrum occurs is achieved in part by preheating the carbon dioxide by conventional gas heating processes and in part by exposing the preheated carbon dioxide to surfaces heated by solar radiation.

3. The method for generating carbon monoxide from carbon dioxide as described in claim 1, wherein said step of cooling the hot gas mixture to stabilize the carbon monoxide is achieved by admixing ambient temperature carbon dioxide into the hot gas mixture.

4. The method for generating carbon monoxide from carbon dioxide as described in claim 3, wherein said step of cooling the hot gas mixture to stabilize the carbon monoxide includes further cooling the admixed hot gas mixture and ambient temperature carbon dioxide using a turbine-based heat removal system.

5. The method for generating carbon monoxide from carbon dioxide as described in claim 3, wherein the carbon dioxide utilized in said step of heating flowing carbon dioxide and said step of admixing ambient temperature carbon dioxide into the hot gas mixture is obtained by extraction from ambient atmospheric gas.

6. The method for generating carbon monoxide from carbon dioxide as described in claim 1, wherein said step of exposing the heated carbon dioxide to solar radiation whereby substantial dissociation of the carbon dioxide takes place is achieved using focused solar radiation.

7. The method for generating carbon monoxide from carbon dioxide as described in claim 6, wherein said step of exposing the heated carbon dioxide to solar radiation whereby substantial dissociation of the carbon dioxide takes place is accomplished by introducing the heated flowing carbon dioxide into a funnel-shaped apparatus in which the focused solar radiation is multiply reflected.

8. The method for generating carbon monoxide from carbon dioxide as described in claim 1, wherein the carbon dioxide in said step of exposing the heated carbon dioxide to solar radiation whereby substantial dissociation of the carbon dioxide takes place is heated to a temperature of greater than 1800 K.

9. The method for generating carbon monoxide from carbon dioxide as described in claim 1, wherein the carbon dioxide in said step of exposing the heated carbon dioxide to solar radiation whereby dissociation of the carbon dioxide takes place is heated such that the absorption cross section of the heated carbon dioxide is greater than $10^{-22}$ cm$^2$ at wavelengths included in the incident solar radiation.

10. The method for generating carbon monoxide from carbon dioxide as described in claim 1, wherein the stabilized carbon monoxide is separated from the carbon dioxide and oxygen present therewith.

* * * * *